United States Patent [19]

Mongeon et al.

[11] Patent Number: 4,728,876
[45] Date of Patent: Mar. 1, 1988

[54] ORTHOPEDIC DRIVE ASSEMBLY

[75] Inventors: Douglas R. Mongeon, Orange, Calif.; Frederick J. Palensky, St. Paul, Minn.

[73] Assignee: Minnesota Mining and Manufacturing Company, Saint Paul, Minn.

[21] Appl. No.: 830,674

[22] Filed: Feb. 19, 1986

[51] Int. Cl.[4] .................................. H02J 7/00
[52] U.S. Cl. .......................... 320/2; 310/50; 318/139; 429/86; 128/92 VT
[58] Field of Search .............. 320/2; 310/50; 429/86, 429/96, 100; 318/139; 128/92 VD, 92 VT, 92 VJ

[56] References Cited

U.S. PATENT DOCUMENTS

| | | | |
|---|---|---|---|
| 3,440,465 | 4/1969 | Pratt et al. | 310/50 |
| 3,909,302 | 9/1975 | Mermelstein | 429/86 |
| 3,973,179 | 8/1976 | Weber et al. | 320/2 |
| 4,081,704 | 3/1978 | Vassos et al. | 310/89 |
| 4,441,563 | 4/1984 | Walton, II | 129/92 VT |

OTHER PUBLICATIONS

Stryker Surgical System, System II Ortho Power 90 Battery Powered Surgical Instruments Maintenance Manual & Operating Instructions and Sales Literature. Dyonics Cordless Surgical Instruments Sales Literature.

*Primary Examiner*—Patrick R. Salce
*Assistant Examiner*—Anita M. Ault
*Attorney, Agent, or Firm*—Donald M. Sell; James A. Smith; William L. Huebsch

[57] ABSTRACT

A cordless rechargeable replaceable battery assembly powered drive assembly for driving orthopedic surgical instruments in which the battery has silver and zinc oxide electrodes in sodium hydroxide electrolyte to provide low voltage high current power. The switch is encased in the battery assembly, the battery cells are vented through a microporous polymeric curtain to restrict expulsion of electrolyte, a two speed transmission is provided to change drive speeds, and a brush block on the motor has contacts adapted to be connected in different combinations to change the motor rotation direction.

30 Claims, 11 Drawing Figures

ORTHOPEDIC DRIVE ASSEMBLY

TECHNICAL FIELD

The present invention relates to cordless rechargeable battery powered drive assemblies for driving orthopedic surgical instruments.

BACKGROUND ART

Cordless rechargeable battery powered drive assemblies for driving orthopedic surgical instruments have been known for many years. Such drive assemblies for example, are presently available from Stryker, Kalamazoo, Mich. as their Series 90 instruments and from Dyonics, Andover, Mass. as their Cordless 200 Reamer or their Cordless 450 Orthopedic Drill. These assemblies utilize batteries having cells containing nickel and cadmium electrodes which store and provide power to an electric direct current activated drive motor in the assembly.

These drive assemblies, however, have not been as convenient to use as might be desired because the combination of the battery chemistry and the direct current motors used in these assemblies does not provide sufficient power to complete many of the procedures undertaken in orthopedic surgery. Thus, batteries must be changed during those procedures which is inconvenient and time consuming.

Also, the rechargeable batteries for these drive assemblies have not been as durable as might be desired due to repeated high temperature (e.g. 270° F.) sterilization in autoclaves required so that the batteries may be used during surgery. Typically the batteries must be replaced after a relatively small number of uses (e.g., 20 to 30) which significantly affects the cost of using the drive assemblies.

DISCLOSURE OF THE INVENTION

The present invention provides a cordless rechargeable battery powered drive assembly for driving orthopedic surgical instruments that can deliver sufficient power from a single charging to complete most orthopedic surgical procedures, and which can withstand a significantly large number of high temperature sterilization cycles in an autoclave (e.g. over 300) without replacement.

According to the present invention there is provided a drive assembly for driving orthopedic surgical instruments of the type comprising a housing, a direct current activated electric drive motor mounted on the housing; a battery mounted on the housing having at least one cell; and a switch assembly including an actuator movable between off and on positions for controlling the flow of electrical power from the battery to the motor.

The advantages described above for the drive assembly according to the present invention are provided because the battery has a plurality of (preferably three) cells containing silver electrodes coated with silver and zinc oxides, and potassium hydroxide electrolyte in which the electrodes are immersed to provide a relatively low electrical potential between terminals of the battery, while affording a relatively high current output (e.g., about 4½ volts while providing a battery with a current output range of about 10 to 70 amps and about 14 amp hours of capacity) and the motor is matched to the low voltage, high potential amperage output of the battery so that it efficiently utilizes the available power.

Preferably the battery has novel vent assemblies mounted in walls defining cavities for the cells in which the electrodes and liquid electrolyte are contained, which vent assemblies each have a passageway between one of the cavities and the atmosphere, means mounted in the passageway for allowing gas in the cavity at a pressure above a predetermined level to escape through the passageway, and a curtain of microporous polymeric material (preferably the polytetrafluoroethylene sheet material sold under the trade designation "Gortex" TM by W. L. Gore Associates, Inc.) extending entirely across the passageway that permits movement of gas through the curtain and passageway while restricting the movement of liquid through the curtain and passageway. Thus the cells will be vented as needed during charging, use or sterilization of the battery, however, the caustic liquid potassium hydroxide electrolyte will not escape during such venting.

Preferably the drive motor is included in a motor assembly and is mounted on a first portion of the housing, the battery is included in a battery assembly and is mounted on a second portion of the housing that provides the majority of the handle for the drive assembly, and means are provided for affording releasable engagement between the motor and battery assemblies and for causing electrical contact between the battery and the motor through the switch assembly. This ability to separate the drive motor and battery facilitates recharging of the battery, and affords easy substitution of a new or charged battery.

The normally open switch assembly in the present invention is of a type especially adapted to switch a large amount of current (e.g., current in the range of 10 to 70 amps) and is preferably included in the battery assembly where it is encased by the second housing portion so that its actuator can not easily be moved to its on position when the battery assembly is separated from the motor assembly. Mounting the switch assembly on the battery assembly insures that the switch will only carry the current output from one battery assembly thereby prolonging its useful life. Encasement of the switch assembly insures that electrically conductive contacts on the battery assembly adapted to engage similar contacts on the motor assembly to electrically connect the battery and drive motor when the battery and motor assemblies are engaged can not normally be shorted out when the battery assembly is separated from the motor assembly.

In a preferred embodiment, the actuator for the switch assembly includes a contact member spaced a first distance from its pivot axis, and an actuating member projecting a second distance substantially greater than the first distance from the axis; a trigger is mounted on the first housing portion of the motor assembly for movement between outer and inner positions, and is biased to the outer position; and the trigger engages an outer end portion of the actuating member to move the actuator from the off to the on position upon movement of the trigger from its outer position to its inner position. This actuator structure allows easy use of the preferred high amperage switch assembly in which the contact member is a conductive blade having a tapered edge and the switch assembly includes spaced conductive spring members each forming a different half of a V-shaped surface. The spring members are adapted to resiliently separate and frictionally receive movement of the tapered edge of the blade therebetween upon movement of the actuator from its off to its on position to help wipe the contact surfaces clean and insure good electrical contact upon each engagement.

In one embodiment, the drive assembly according to the present invention includes manually activatable means for axially shifting an output shaft of the drive motor relative to the first housing portion between first and second positions; and transmission means between the motor and a drive member adapted to drive surgical instruments, which transmission means is engaged by the output shaft in either of its first and second positions for driving the drive member at a first drive ratio (e.g., about 5.37 to 1) when the output shaft is in its first position, and for driving the drive member at a second different drive ratio (e.g., about 28.82 to 1) when the output shaft is in the second position.

Also, one embodiment of the drive assembly according to the present invention includes a brush holder around a rotor commutator having a ring of contacts alternately connected to the battery or to the brushes; and a switch plate mounted on the housing for rotational movement around the axis between first and second positions and carrying conductive plates that bridge the contacts to connect the brushes to the battery to cause rotation of the rotor in one direction when the switch plate is in the first position, bridge the contacts to reverse the polarity of the brushes and cause rotation of the rotor in the opposite direction when the switch plate is in the second position, and do not bridge any contacts in a position of the switch plate between its first and second position so that the motor can not be operated.

BRIEF DESCRIPTION OF THE DRAWING

The present invention will be further described with reference to the accompanying drawing wherein like numbers refer to like parts in the several views, and wherein.

DETAILED DESCRIPTION OF THE PREFERRED EMBODIMENT

Figure 1:
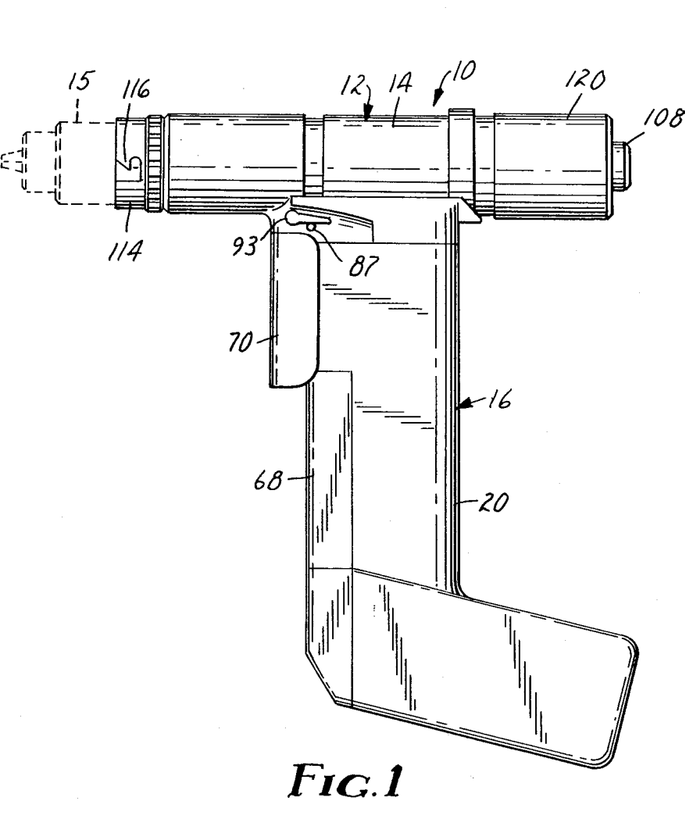
FIG. 1 is a side view of a cordless rechargeable battery powered drive assembly according to the present invention.
Figure 2:
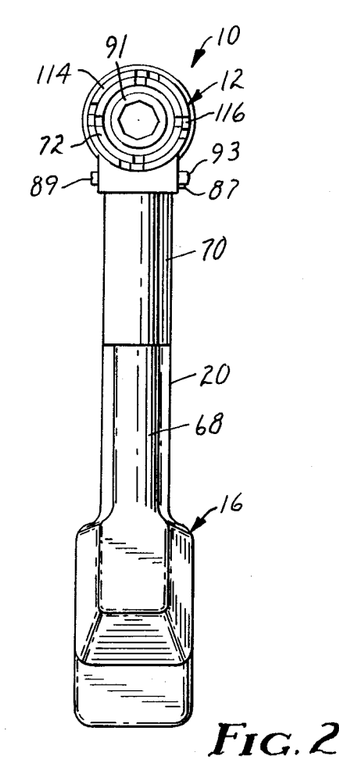
FIG. 2 is a front view of the drive assembly of FIG. 1.
Figures 7, 8, 9, 10:
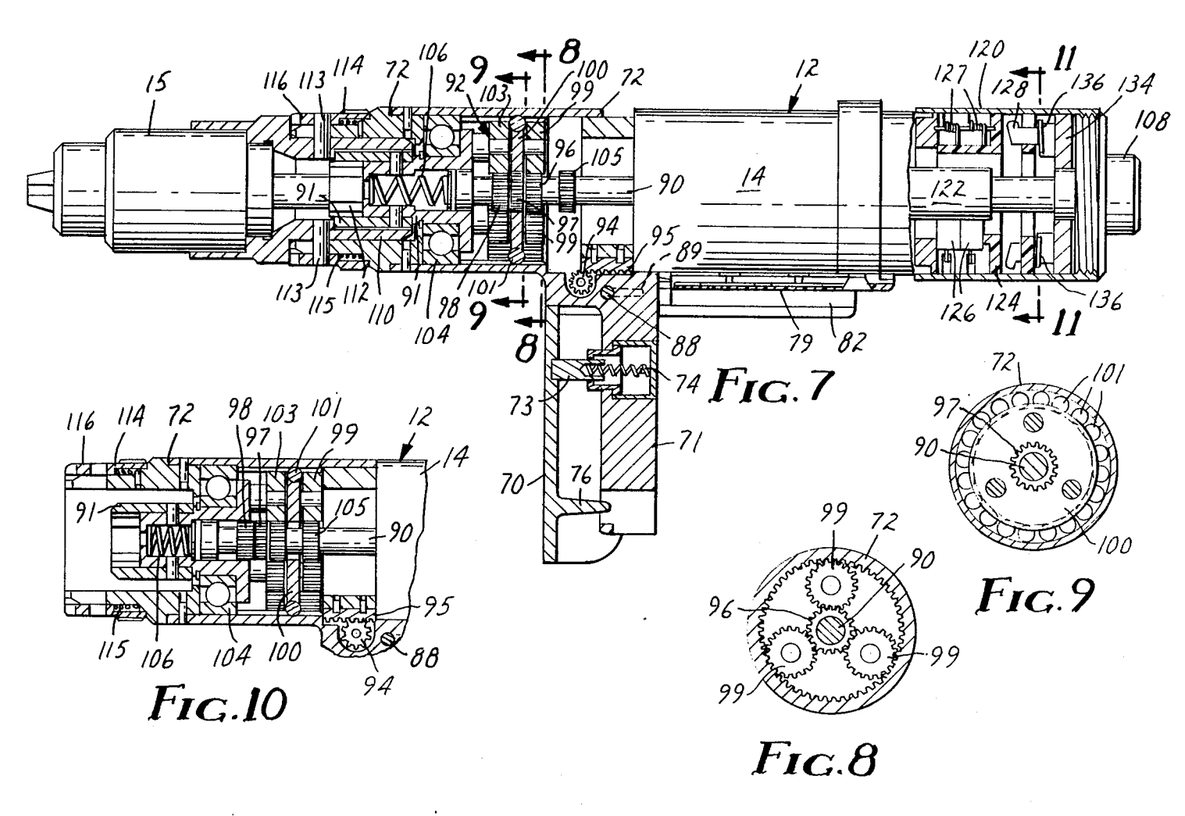
FIG. 7 is an enlarged side view, mostly in section, of a motor assembly included in the drive assembly shown in FIG. 1 with a transmission in the motor assembly in a first position.
FIG. 8 is a sectional view taken approximately along line 8—8 of FIG. 7.
FIG. 9 is a sectional view taken approximately along line 9—9 of FIG. 7.
FIG. 10 is a fragmentary view of the motor assembly of FIG. 7 shown with the transmission in a second position.

Referring now to the drawing there is shown a cordless rechargeable battery powered drive assembly 10 (FIGS. 1 and 2) which drive assembly 10 includes a motor assembly 12 (FIGS. 1, 2 and 7-10) including a D.C. electric powered motor 14 adapted to engage various orthopedic surgical instruments either directly or through a drive chuck such as the drive chuck 15 shown in phantom in FIG. 1 and in solid outline in FIG. 7, and a rechargeable battery assembly 16 (FIGS. 1-6) which provides the majority of the handle for the drive assembly 10, is adapted to releasably engage and provide a rechargeable source of power for the motor 14, and includes a switch assembly 18 for controlling the flow of electrical power from the battery assembly 16 to the motor 14.

As is best seen in FIGS. 3-6, the rechargeable battery assembly 16 comprises a second portion 20 of the housing for the drive assembly 10, a battery mounted on the second housing portion 20 having at least one, and as illustrated, three, cells 22 (one cell 22 disposed in a hand grip portion of the battery assembly 16, and two cells 22 disposed side by side in a butt portion of the battery assembly 16) connected in series by two electrically conductive strips 24 and 26 attached by bolts 28 to the cells 22 to provide an electrically negative terminal 30 at an upper end of the battery assembly 16 and an electrically positive terminal 32 adjacent the switch assembly 18.

Figures 3, 4:
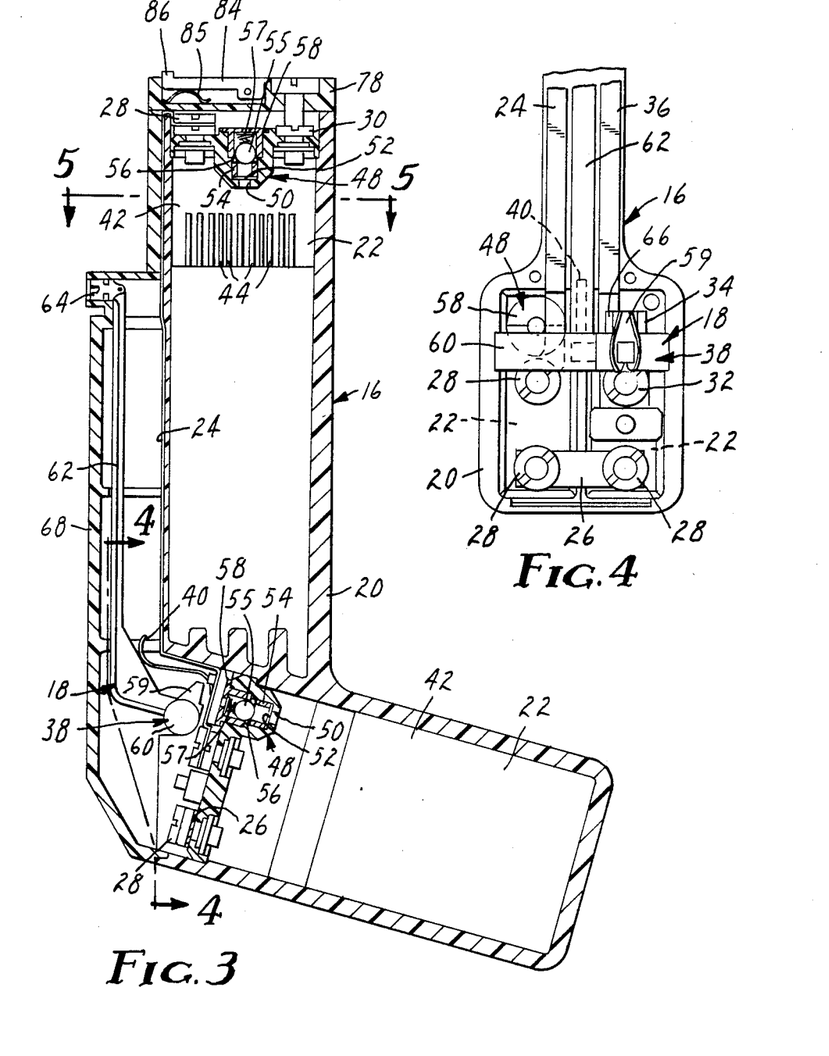
FIG. 3 is an enlarged sectional side view of a battery assembly included in the drive assembly shown in FIG. 2.
FIG. 4 is a sectional view taken approximately along line 4—4 of FIG. 3.
Figure 5:
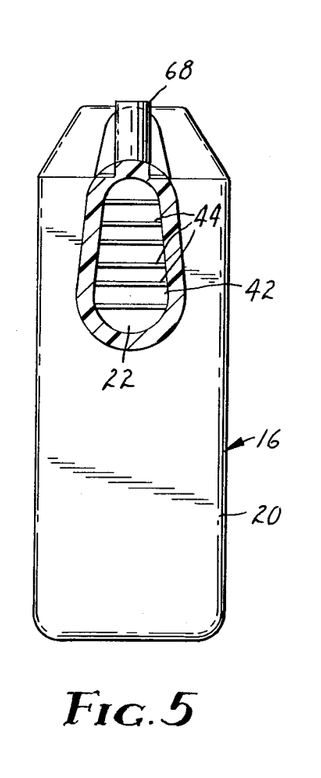
FIG. 5 is a sectional view taken approximately along line 5—5 of FIG. 3.

The switch assembly 16 has an input lead 34 coupled to the terminal 32, an output lead 36 extending to the upper end of the battery assembly 16 and means including an actuator 38 movable relative to the second housing portion 20 between off and on positions for making an electrical connection between the input and outlet leads 34 and 36 when the actuator 38 is in its on position, and for causing those leads 34 and 36 to be electrically isolated from each other when said actuator 38 is in its off position. Means in the form of a leaf spring 40 are also provided for biasing the actuator 38 to its off position.

Each cell 22 of the battery assembly 16 comprises walls of the second housing portion 20 defining a cavity 42, and electrodes 44 in the cavity 42 immersed in a 40% concentration in water of potassium hydroxide. The electrodes comprise interconnected silver screen electrodes (e.g., 5 electrodes) coated with silver oxide powder and wrapped with cellophane sheets (positive electrodes) closely interdigitated between interconnected silver screen electrodes (e.g., 6 electrodes) coated with zinc oxide powder and also wrapped in cellophane sheets (negative electrodes). These three cells 22 provide an electrical potential between the terminals 30, 32 of about 4½ volts and provide a battery assembly 16 capable of current output in the range of 10 to 70 amps with about 12 amp hours of capacity.

The battery assembly 16 also includes novel vent assemblies 48 (FIG. 3) in the walls defining the cavities 42, which vent assemblies 48 provide passageways 50 between the cavities 42 and the atmosphere, means mounted in the passageways 50 for allowing gas in the cavities 42 at a pressure above a predetermined level to escape through the passageways 50, and curtains 52 of microporous polymeric material entirely across the passageways 50 that permit movement of gas through the curtains 52 and passageways 50 while restricting the movement of liquid through the curtains 52 and passageways 50.

As is best seen in FIG. 3, each vent assembly 48 comprises a socket formed in the walls defining the adjacent cavities 42 with a through opening at its inner end, a hollow cylindrical bushing 54 press fit into an inner portion of the socket to hold the curtain 52 across the through opening and a ball 55 pressed against an O-ring 56 overlying the bushing 54 by a coil spring 57 held against the ball 55 by a hollow retaining bushing 58 threadably engaged with the second housing portion 20 and also having a through central opening. When the pressure in the cells 22 exceeds a predetermined pressure (e.g., 5 to 7 psi) that pressure will lift the ball 55 from the O-ring 56 and allow the gas to escape through the passageway 50. The curtain 52 is of a microporous polymeric material (e.g., preferably polytetrafluoroethylene sheet material because of its resistance to chemicals and high temperature resistance, such as that commercially designated "Gortex" TM available from W. L. Gore and Associates, Inc., Newark, Del.) preferably backed for physical support on its side opposite the cell 22 by a screen-like grid of the same material. The curtain 52 allows such gas to pass through the vent assembly 48, but will not permit the passage of the liquid electrolyte. As illustrated, one vent assembly 48 is provided for the cell 22 in the handgrip portion of the battery assembly 16, and a second vent assembly 48 is provided to vent both of the cells 22 in the butt portion of the battery assembly 16, the cavities 42 of which are interconnected.

The actuator 38 of the switch assembly 18 seen in FIGS. 3 and 4 comprises a contact member 59 which is mounted to project a first distance radially from a shaft 60 mounted transverse of the second housing portion 20 for pivotal movement about its axis between the off and on positions of the actuator 38, and an L-shaped actuating member 62 projecting a second distance from the axis, which second distance is substantially greater than the distance the actuator 38 projects from the axis. The actuating member 62 has an outer end portion opposite the axis to which is pivotably attached a cup-like member 64 having a socket opening through its distal end. The contact member 59 is conductive and has a tapered edge. The switch assembly further includes opposed conductive spring members (e.g. of beryllium copper), one of which is the input lead 34, and the other of which, spring member 66, is attached at the adjacent end of the output lead 36. The spring members 34 and 66 have adjacent surfaces disposed to form a V-shaped surface therebetween generally corresponding to the tapered edge of the contact member 59 and are adapted to be resiliently separated and to frictionally receive the tapered edge of the contact member 59 to electrically connect the spring members 34 and 66 upon movement of the actuator 38 from its off to its on position. The long length of the actuating member 62 relative to that of the contact member 59 (e.g., 10 to 1 ratio) allows a significantly large force to be applied to force the contact member 59 into engagement with and between the spring members 34 and 66 from a relatively small application of force at the outer end of the actuating member 62. Such force helps to positively switch the relatively large current flow (i.e., 10 to 70 amps) produced by the cells 22 which is further facilitated by the relatively large surface contact between the mating surfaces of the contact member 59 and the spring members 34 and 66; and the resultant small spacing between the contact member 59 and the spring members 34 and 66 when the actuator 38 is in its off position is acceptable due to the relatively small voltage potential that is being switched (i.e. 4½ volts).

The second housing portion 20 includes a cover 68 completely encasing the actuator 38 except for a small opening leading to a cylindrical passageway in which the cup-like member 64 is guided. Thus, the actuator 38 will normally be in its off position under the influence of the spring 40 when the battery assembly 16 is removed from the motor assembly 12, and can not then easily be inadvertently moved to its on position so that inadvertent shorting of exposed contact plates 80 and 81 connected respectively to the battery terminal 30 and the output lead 36 on the upper end of the battery assembly 16 is restricted. The actuator 38 can, however, be easily moved to its on position when the battery assembly 16 is attached to the motor assembly 12 by manual manipulation of a trigger 70 on the motor assembly 12.

As is best seen in FIG. 7, the trigger 70 is an elongate arcuate member extending along a projection 71 which is part of a first housing portion 72 included in the motor assembly 12. The trigger 70 has an upper inwardly extending post 73 slidably mounted in a socket on that projection 71 for movement between an outer position to which the trigger 70 is biased by a spring 74, and an inner position, and has a pin 76 adjacent its end opposite the motor 14 which projects into a channel in the projection 71. When the motor assembly 12 and battery assembly 16 are attached, part of the second housing portion 20 defining the cylindrical passageway in which the cup-like member 64 is guided is positioned in that channel so that a distal end of the pin 76 is positioned in the socket in the cup-like member 64 attached to the end of the actuating member 62. Manual movement of the trigger 70 to its inner position will then cause corresponding movement of the actuator 38 to its on position through that contact, whereas the springs 74 and 40 will normally position the trigger 20 and actuator 38 in their outer and off positions respectively.

Figure 6:
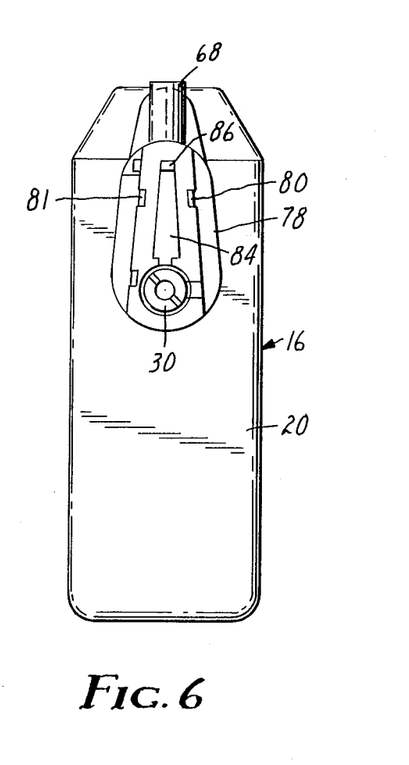
FIG. 6 is a top view of the battery assembly shown in FIG. 3.

The means for releasably engaging the battery assembly 16 with the motor assembly 12 is best seen in FIGS. 3, 6 and 7. At the upper end of the second housing portion 20 of the battery assembly 16 is a dovetail projection 78 tapered outwardly toward its distal end and increasing in width toward the side of the handle portion of the battery assembly 16 opposite the actuator 38. The electrically conductive contact plates 80 and 81, connected respectively to the terminal 30 of the battery and the output lead 36 of the switch assembly 18, are positioned along opposite sides of the projection 78. A mating socket 79 for the projection 78 is formed on the motor assembly adjacent the side of the projection 71 opposite the trigger 70 and has two opposed contact plates 82 connected to the motor 14. The socket 79 receives the dovetail projection 78 as it is slid toward the projection 71 to bring the contact plates 80, 81 and 82 into firm electrical contact. A latch 84 is pivotably mounted on the second housing portion 20 and is biased by a spring 85 to a position with a projection 86 on the latch 84 projecting above the distal surface of the dovetail projection 78 so that when that dovetail projection 78 is fully engaged with the socket in the motor assembly 12, the projection 86 will drop into an opening in the first housing portion 72 to retain that engagement. The motor assembly 12 has a release lever assembly 88 including a shaft on which is mounted a release lever 89 manually accessible from the side of the first housing portion 72 opposite that shown in FIG. 7, and an inner release portion (not shown) that can be pivoted by manual manipulation of the release lever 89 to push the projection 86 from the recess and allow separation of the motor assembly 12 and battery assembly 16. The release lever assembly 88 is biased axially of the shaft by a spring (not shown) to a position with the release lever 89 in a recess on the side of the first housing portion 72 to restrict inadvertent movement of the release lever assembly 89 to release the battery assembly 16. The release lever 89 can be pivoted to release the battery assembly 16, however, by pressing a projecting portion 77 of the shaft opposite the release lever 89 into the first housing portion 72 and thereby the release lever 89 out of the recess while the release lever 89 is simultaneously pivoted to release the battery assembly 16.

The motor 14 in the drive assembly 10 is designed to (1) operate at about 3.7 volts which is about the voltage to which the output from battery assembly 16 will drop when the motor 14 is under load, (2) to have very low internal resistance to minimize internal losses when handling the high current flow by which it is powered, and (3) to produce about 0.149 horsepower at 5200 RPM (about 70% of free speed) from an input of 3.7 volts and 50 amps.

The drive assembly also includes means shown in FIGS. 7–10 for producing two drive speeds from the single speed D.C. motor 14, which means comprises manually actuatable means for axially shifting an output shaft 90 on the motor 14 relative to the first housing portion 72 between a first position (FIG. 7) and a second position (FIG. 10); a drive member 91 rotatably mounted on the first housing portion 72 at an axially fixed position, which drive member 91 is adapted to releasably engage surgical instruments (e.g., dills, reamers, saws, wires) either directly or through holders such as the drive chuck 15; and transmission means 92 between the motor 14 and the drive member 91 coupled to the drive member 91, and engaged by the output shaft 90 in either of its first or its second positions for driving the drive member 91 at a first drive ratio when the output shaft 90 is in its first position (FIG. 7), and for driving the drive member 91 at a second drive ratio different than the first drive ratio when the output shaft 90 is in its second position (FIG. 10).

The means for axially shifting the output shaft 90 is provided in that the entire motor 14 including its housing is mounted on the first housing portion 72 for axial movement to shift the output shaft 90 between its first and second positions with the motor 14 being shiftable between those positions by manual movement of a lever 93 that drives a pinion 94 engaged with a rack 95 formed on the motor housing.

The motor shaft carries a drive gear 96 fixed on the output shaft 90 adjacent its proximal end and two idler gears 97 and 98 fixed together and rotatably mounted on the output shaft 90 adjacent its distal end. In the first position of the motor shaft 90 (FIG. 7), the drive gear 96 is positioned to drive a first planetary gear assembly including three spaced planetary gears 99 rotatably mounted on shafts projecting from a plate 100, which plate is mounted by bearing balls 101 around its periphery for rotation within the first housing portion 72 with each planetary gear 99 in engagement with both the drive gear 96 and a ring gear formed around the inside of the first housing portion 72. Rotation of the planetary gears 99 by the drive gear 96 causes the plate 100 to revolve at a speed less than that of the output shaft 90 (e.g., about a 5.37 to 1 reduction). The plate 100 has a central opening having inwardly projecting teeth adapted to engage the idler gear 97 which is positioned within and is driven by the plate 100, and the idler gear 98 fixed to the idler gear 97 drives a second planetary gear assembly also including three planetary gears 103 mounted by shafts projecting from the drive member 91 (which drive member 91 is rotatably mounted in the second housing portion by a ball bearing 104) with each planetary gear 103 in engagement with a ring gear formed around the inside of the first housing portion 72. Rotation of the planetary gears 103 by the plate 100 driven idler gear 98 will also cause the drive member 91 to revolve at a speed less than that of the idler gears 97 and 98 causing a second speed reduction (e.g., also about a 5.37 to 1 reduction) within the transmission means 92, for a total speed reduction through the transmission means 92 of about 28.82 to one.

In the second position of the output shaft 90 (FIG. 10) the drive gear 96 is positioned within and directly drives the planetary gears 103 of the second planetary gear assembly so that only the speed reduction through that second planetary gear assembly has any effect on the speed of the drive member 91. An alignment gear 105 fixed on the output shaft 90 moves within and drives the planetary gears 99 of the first planetary gear assembly and the plate 100, however, there is no connection between the plate 100 and the second planetary gear assembly so that the first planetary gear assembly and the plate 100 are not part of the gear train to the drive member 91. The only function of the alignment gear 105 is to maintain proper orientation of the planetary gears 99 in the first planetary gear assembly for subsequent re-engagement by the drive gear 96 when the output shaft 90 is again moved to its first position. Such return movement of the output shaft 90 to its first position is facilitated by a coil spring 106 between the distal end of the shaft 90 and the drive member 91.

The drive member 91, output shaft 90 and an end cap 108 on the motor housing have aligned central through openings that afford inserting a wire through the motor assembly 12 and into the proximal end of a wire driver (not shown) engaged with the drive member 91 so that the wire can be driven by the wire driver during orthopedic procedures.

The means for attaching the illustrated chuck 15 or such other holders or instruments that may be driven by the drive assembly (e.g., saws, wire drivers, etc.) comprises a socket into which a cylindrical portion 110 of the chuck 15 or other instrument can project with a splined central rotatable driven collar engaged with mating splines on the inner surface of the drive member 91, and with pins 113 projecting radially of the cylindrical portion engaged in longitudinally extending slots opening through the end of the first housing portion 72. A collar 114 rotatable about the first housing portion is then biased by a spring 115 so that circumferentially projecting hooks 116 on the collar 114 (FIG. 1) can engage the pins 113 to maintain the pins 113 within the slots and thereby the chuck 15 or other holders or instruments in driven engagement with the drive assembly 10.

The drive assembly 10 also includes a convenient switch means, operated by rotating a fluted cup-like member 120 on the end of the motor assembly 12 opposite the drive member 91, for causing the motor 14 to rotate the drive member 91 either in forward or reverse directions, or to prevent any rotation by the motor 14 when the trigger 70 is moved to its inner position. The rotor in the drive motor 14 has a commutator 122 (FIGS. 7 and 11), a brush holder 124 fixed relative to the motor housing and thereby relative to the first housing portion 72 around the commutator 122, and a plurality of brushes 126 mounted on the brush holder and biased by springs 127 into contact with the commutator 122. The brush holder 124 has a ring of spaced contacts 128, sequentially connected (when the switch assembly is on) to the positive terminal of the battery, to one set of brushes 126, to the negative terminal of the battery, to the next set of brushes 126, to the positive terminal of the battery, to the next set of brushes, to the negative terminal of the battery, and to the last set of brushes. A switch plate 134 is mounted in the cup-like member 120 for limited rotational movement with that member 120 around the axis of the rotor between first and second positions. The switch plate 134 includes means in the form of 4 arcuate conductive connecting plates 136 shown in phantom in FIG. 11, spring loaded toward the contacts 128 to connect the brushes 126 to the battery to cause rotation of the rotor in one direction when the switch plate 134 is in its first position, and for connecting the brushes 126 to the battery to cause rotation of the rotor in the opposite direction when the switch plate 134 is in its second position. This occurs because in the first position of the switch plate 134 the connecting plates 136 connect two sets of brushes to contacts 128 connected to the positive terminal of the battery and two other sets of the brushes 126 to the contacts connected to the negative terminal of the battery, and in the second position of the switch plate 134 the connecting plates 136 connect each set of brushes to contacts 128 connected to the opposite terminal of the battery.

Figure 11:
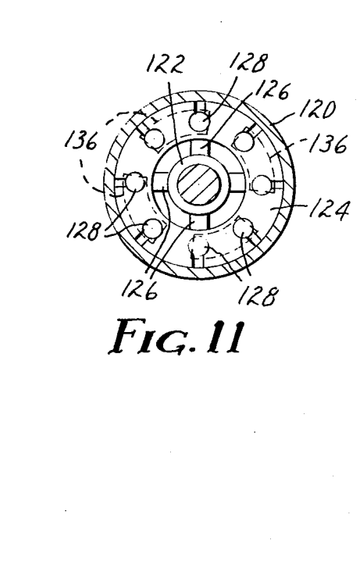
FIG. 11 is a sectional view taken approximately along line 11—11 of FIG. 7.

Also, the contacts 128 are spaced so that in an intermediate position of the switch plate 134 between its first and second positions, the connecting plate 136 will contact only the contacts 128 connected to the brushes thereby preventing electrical current from flowing through the brushes 126 and any rotation of the armature.

The present invention has now been described with reference to one embodiment thereof. It will be apparent to those skilled in the art that many changes can be made in the embodiment described without departing from the scope of the present invention. For example, the drive assembly can be made in alternate embodiments in which there is no transmission means so that the drive member is connected directly to the output shaft of the motor. Also, the motor can be made to rotate only in one direction so that the brushes are directly wired and the contacts 128 and contact plate 134 are not required. Additionally, the vent assemblies 48 may be useful with batteries having many different chemistries, such as nickel-cadmium batteries, and for some chemistries other microporous polymeric material other than may be useful where the requirements for chemical and temperature resistance are not as severe as for the application described above. Thus the scope of the present invention should not be limited to the structures described in this application, but only by structures described by the language of the claims and the equivalents of those structures.

We claim:

1. A drive assembly for driving orthopedic surgical instruments, said drive assembly comprising:
    a first housing portion;
    an electric direct current activated motor mounted on said first housing portion and having positive and negative electric power contacts;
    a second housing portion;
    a battery mounted on said second housing portion having at least one cell and electrically positive and negative terminals, said cell comprising walls defining a cavity, electrodes electrically coupled to said terminals within said cavity, a liquid electrolyte within said cavity and in which said electrodes are immersed to provide an electrical potential between said terminals, and a vent assembly mounted in said walls, said vent asssembly having a passageway between said cavity and the atmosphere, means mounted in said passageway for allowing gas in said cavity at a pressure above a predetermined level to escape through said passageway, and a curtain of microporous polymeric material entirely across said passageway that permits movement of gas though said curtain and passageway while restricting the movement of liquid through said curtain and passageway;
    a switch assembly mounted on said second housing portion having an input lead coupled to one of said terminals, an output lead, and means including an actuator movable relative to said second housing portion between off and on positions for making an electrical connection between said input and outlet leads when said actuator is in said one position and for causing said leads to be electrically isolated from each other when said actuator is in said off position, and means for biasing said actuator to said off position; and
    means for affording releasing engagement between said first and second housing portions and for causing electrical contact between one of said power contacts and the output lead of said switch assembly and between the other of said power contacts and the other of said terminals.

2. A drive assembly according to claim 1 wherein said battery has threee cells with electrodes comprising silver and zinc oxides electrically coupled to said terminal, and potassium hydroxide electrolyte in which said electrodes are immersed to provide an electrical potential between said terminals of about 4½ volts and provide a battery with a current output range of about 10 to 70 amps and about 14 amp hours of capacity.

3. A drive assembly according to claim 1 wherein said battery has a plurality of cells with potassium hydroxide electrolyte in the cavities of said cells, and one of said vent assemblies connected to each of said cells.

4. A drive assembly according to claim 1 wherein said curtain comprises polytetrafluoroethylene.

5. A drive assembly according to claim 1 wherein said motor comprises a rotor rotatable about an axis and comprising a commutator, a brush holder fixed relative to said first housing portion around said commutator, a plurality of brushes mounted on said brush holder and contacting said commutator, said brush holder having a ring of contacts alternatively connected to the battery and to the brushes, and a switch plate mounted on said first housing portion for rotational movement around said axis between first and second positions, said switch plate including means for connecting said brushes to said battery to cause rotation of said rotor in one direction when said switch plate is in said first position, and for connecting said brushes to said battery to cause rotation of said rotor in the opposite direction when said switch plate is in the said second position.

6. A drive assembly for driving orthopedic surgical instruments, said drive assembly comprising:
   a first housing portion;
   an electric direct current activated motor mounted on said first housing portion and having positive and negative electric power contacts;
   a second housing portion;
   a battery mounted on said second housing portion having at least one cell and electrically positive and negative terminals;
   a switch assembly mounted on said second housing portion having an input lead coupled to one of said terminals, an output lead, and means including an actuator movable relative to said second housing portion between off and on positions for making an electrical connection between said input and outlet leads when said actuator is in said on position and for causing said leads to be electrically isolated from each other when said actuator is in said off position, and means for biasing said actuator to said off position, said actuator being mounted for pivotal movement about an axis between said off and on positions, including a contact member spaced a first distance from said axis, and an actuating member projecting a second distance substantially greater than said first distance from said axis, which actuating member has an outer end portion opposite said axis;
   a trigger mounted on said first housing portion for movement between outer and inner positions said trigger engaging the outer end portion of said actuating member to move said actuator from said off to said on position upon movement of said trigger from said outer position to said inner position;
   means for biasing said trigger to said outer position; and
   means for affording releasable engagement between said first and second housing portions and for causing electrical contact between one of said power contacts and the output lead of said switch assembly and between the other of said power contacts and the other of said terminals.

7. A drive assembly according to claim 6 wherein said contact member is a conductive blade having a tapered edge and said switch assembly further includes opposed spring members each defining half of a generally V-shaped surface adapted to resiliently separate and frictionally receive movement of the conductive blade therebetween tapered edge first upon movement of said actuator from its off to its on position.

8. A drive assembly according to claim 6 wherein said actuating member is encased by said second housing portion, said trigger has a projection adapted to engage the end portion of said actuator, and said second housing portion has an opening to afford engagement of said projection with said end portion.

9. A drive assembly for driving orthopedic surgical instruments, said drive assembly comprising:
   a first housing portion;
   an electric direct current activated motor mounted on said first housing portion and having positive and negative electric power contacts, said motor comprising a a rotor rotatable about an axis and including an axially projecting output shaft;
   manually activatable means for axially shifting said output shaft relative to said first housing portion between first and second positions;
   a drive member rotatably mounted on said first housing portion at an axially fixed position, said drive member being adapted to releasably engage a surgical instrument;
   transmission menas between said motor and said drive member coupled to said drive member, and engaged by said output shaft in either of said first and second positions for driving said drive member at a first drive ratio when said outpt shaft is in said first position, and for driving said drive member at a second drive ratio different than said first drive ratio when said output shaft is in said second position;
   a second housing portion;
   a battery mounted on said second housing portion having at least one cell and electrically positive and negative terminals;
   a switch assembly mounted on said second housing portion having an input lead coupled to one of said terminals, an output lead, and means including an actuator movable relative to said second housing portion between off and on positions for making an electrical connection between said input and outlet leads when said actuator is in said one position and for causing said leads to be electrically isolated from each other when said actuator is in said off position, and means for biasing said actuator to said off position; and
   means for affording releasable engagement between said first and second housing portions and for causing electrical contact between one of said power contacts and the output lead of said switch assembly and between the other of said power contacts and the other of said terminals.

10. A drive assembly for driving orthopedic surgical instruments, said drive assembly comprising:
    a housing;
    an electric direct current activated motor mounted on said housing and having positive and negative electric power contacts;
    a battery mounted on said housing having at least one cell with electrodes comprising silver and zinc oxides electrically coupled to electrically positive and negative terminals, with one of said terminals coupled to one of said contacts and potassium hydroxide electrolyte in which said electrodes are immersed to provide an electrical potential between said terminals;
    a switch assembly mounted on said housing having an input lead coupled to the other of said terminals, an output lead coupled to the other of said contacts, and means including an actuator movable relative to said housing between an off and an on position for making an electrical connection between said input and outlet leads when said actuator is in said on position and for causing said leads to be electrically isolated from each other when said actuator is in said off position, and means for biasing said actuator to said off position.

11. A drive assembly according to claim 10 wherein said battery has three cells with electrodes comprising silver and zinc oxides electrically coupled to said terminal, and potassium hydroxide electrolyte in which said electrodes are immersed to provide an electical potential betweeen said terminals in the range of about 4½ volts and provide a battery with a current output range of about 10 to 70 amps and about 14 amp hours of capacity.

12. A drive asembly according to claim 10 wherein said cell comprises walls defining a cavity, with said electrodes electrically coupled to said terminals and said liquid electrolyte within said cavity, and a vent assembly mounted in said walls, said vent assembly having a passageway between said cavity and the atmosphere, means mounted in said passageway for allowing gas in said cavity at a pressure above a predetermined level to escape through said passageway, and a curtain of micro porous polymeric material across said passageway that permits movement of gas through said curtain and passageway while restricting the movement of liquid through said curtain and passageway.

13. A drive assembly according to claim 12 wherein said battery has a plurality of cells with potassium hydroxide electrolyte in the cavities of said cells, and one of said vent assemblies connected to each of said cells.

14. A drive assembly according to claim 12 wherein said curtain comprises polytetrafluorethylene.

15. A drive assembly according to claim 10 wherein said actuator is mounted for pivotal movement about an axis between said off and on positions, includes a contact member spaced a first distance from said axis, and an actuating member projecting a second distance substantially greater than said first distance from said axis which actuating member has an outer end portion opposite said axis; said drive assembly includes a trigger mounted on said housing for movement between outer and inner positions, and means for biasing said trigger to said outer position; and said trigger engages the outer end portion of said actuating member to move said actuator from said off to said on position upon movement of said trigger from said position outer to said inner position.

16. A drive assembly according to claim 15 wherein said contact member is a conductive blade haivng a tapered edge and said switch assembly further includes opposed spring members each defining half of a generally V-shaped surface adapted to resiliently separate and frictionally receive movement of the conductive blade therebetween tapered edge first upon movement of said actuator from its off to its on position.

17. A drive assembly according to claim 10 wherein said motor comprises a rotor rotatable about an axis and including an axially projecting output shaft; and said drive assembly further includes manually activatable means for axially shifting said output shaft relative to said first housing portion between first and second positions; a drive member rotatably mounted on said first housing portion at an axially fixed position, said drive member being adapted to releasably engage a surgical instrument; and transmission means between said motor and said drive member coupled to said drive member, and engaged by said output shaft in either of said first and second positions for driving said drive member at a first drive ratio when said output shaft is in said first position, and for driving said drive member at a second drive ratio different than said first drive ratio when said output shaft is in said second position.

18. A drive assembly according to claim 17 wherein one of said drive ratios is about 5.37 to 1 and the other of said drive ratios is about 28.82 to 1.

19. A drive assembly according to claim 10 wherein said drive motor comprises a rotor rotatable about an axis and comprising a commutator, a brush holder fixed relative to said housing around said commutator, a plurality of brushes mounted on said brush holder and contacting said commutator, said brush holder having a ring of contacts alternatively connected to the battery and to the brushes, and a switch plate mounted on said first housing portion for rotational movement around said axis between first and second positions, said switch plate including means for connecting said brushes to said battery to cause rotation of said rotor in one direction when said switch plate is in said first position, and for connecting said brushes to said battery to cause rotation of said rotor in the opposite direction when said switch plate is in said second position.

20. A rechargeable battery assembly adapted for use on a drive assembly for driving orthopedic surgical instruments, which drive assembly comprises a first housing portion; and an electric direct current activated motor mounted on said first housing portion and having positive and negative electric power contacts, said battery pack comprising:

a second housing portion;
a battery mounted on said second housing portion having at least one cell and electrically positive and negative terminals; said cell comprising walls defining a cavity, electrodes electrically coupled to said terminals within said cavity, a liquid electrolyte within said cavity and in which said electrodes are immersed to provide an electrical potential between said terminals, and a vent assembly mounted in said walls, said vent assembly having a passageway between said cavity and the atmosphere, means mounted in said passageway for allowing gas in said cavity at a pressure above a predetermined level to escape through said passageway, and a curtain of microporous polymeric material across said passageway that permits movement of gas through said curtain and passageway while restricting the movement of liquid through said curtain and passagway; and
means adapted for affording releasable engagement of said second housing portion with said first housing portion and for affording electrical contact between said power contacts and said terminals.

21. A battery assembly according to claim 20 wherein said battery has three cells with electrodes comprising silver and zinc oxides electrically coupled to said terminal, and potassium hydroxide electrolyte in which said electrodes are immersed to provide an electrical potential between said terminals of about $4\frac{1}{2}$ volts and provide a battery with a current output range of about 10 to 70 amps and about 14 amp hours of capacity.

22. A battery assembly according to claim 20 wherein said battery has a plurality of cells with potassium hydroxide electrolyte in the cavities of said cells, and one of said vent assemblies connected to each of said cells.

23. A battery assembly according to claim 20 wherein said curtain comprises polytetrafluoroethylene.

24. A rechargeable battery assembly adapted for use on a drive assembly for driving orthopedic surgical instruments, which drive assembly comprises a first housing portion; and an electric direct current activated motor mounted on said first housing portion and having positive and negative electric power contacts, said battery pack comprising:

a second housing portion;
a battery mounted on said second housing portion having at least one cell and electrically positive and negative terminals;

a switch assembly mounted on said second housing portion having an input lead coupled to one of said terminals, an output lead, and means including an actuator movable relative to said second housing portion between off and on positions for making an electrical connection between said input and outlet leads when said actuator is in said on position and for causing said leads to be electrically isolated from each other when said actuator is in said off position, and means for biasing said actuator to said off position, said actuator being mounted for pivotal movement about an axis between said off and on positions, including a contact member spaced a first distance from said axis, and an actuating member projecting a second distance substantially greater than said first distance from said axis, which actuating member has an outer end portion opposite said axis; said housing encasing said actuator and having an opening affording engagement of the outer end portion of said actuating member to move said actuator from said off to said one position; and means adapted for affording releasable engagment of said second housing portion with said first housing portion and for causing electircal contact between one of said power contacts and the output lead of said switch assembly and between the other of said power contacts and the other of said terminals.

25. A battery assembly according to claim 24 wherein said contact member is a conductive blade having a tapered edge and said switch assembly further includes opposed spring members each defining half of a generally V-shaped surface adapted to resiliently separate and frictionally receive movement of the conductive blade therebetween tapered edge first upon movement of said actuator from its off to its on position.

26. A drive assembly for driving orthopedic surgical instruments comprising a housing; a motor including a rotor rotatable about an axis and including an axially projecting output shaft; a manually activatable means for axially shifting said output shaft relative to said housing between first and second positions; a drive member rotatably mounted on said housing at an axially fixed position, said drive member being adapted to releasably engage a surgical instrument; and transmission means between said motor and said drive member coupled to said drive member, and engaged by said output shaft in either of said first and second positions for driving said drive member at a first drive ratio when said output shaft is in said first position, and for driving said drive member at a second drive ratio different than said first drive ratio when said output shaft is in said second position.

27. A drive assembly according to claim 26 wherein one of said drive ratios is about 5.37 to 1.

28. A battery comprising a cell including walls defining a cavity, electrodes electrically coupled to said terminals within said cavity, a liquid electrolyte within said cavity and in which said electrodes are immersed to provide an electrical potential between said terminals, and a vent assembly mounted in said walls, said vent assembly having a passageway between said cavity and the atmosphere, means mounted in said passageway for allowing gas in said cavity at a pressure above a predetermined level to escape through said passageway, and a curtain of microporous polymeric material entirely across said passageway that permits movement of gas through said curtain and passageway while restricting the movement of liquid through said curtain and passageway.

29. A battery according to claim 28 wherein said battery has a plurality of cells with potassium hydroxide electrolyte in the cavities of said cells, and one of said vent assemblies connected to each of said cells.

30. A battery according to claim 28 wherein said curtain comprises polytetrafluoroethylene.

* * * * *

UNITED STATES PATENT AND TRADEMARK OFFICE
CERTIFICATE OF CORRECTION

PATENT NO. : 4,728,876

DATED : March 1, 1988

INVENTOR(S) : Douglas R. Mongeon and Frederick J. Palensky

It is certified that error appears in the above-identified patent and that said Letters Patent is hereby corrected as shown below:

Column 10, line 29, "one" should read --on--.

Column 12, line 27, "one" should read --on--.

Column 15, line 21, "one" should read --on--.

Column 15, line 25, "electircal" should read --electrical--

Signed and Sealed this

Seventh Day of March, 1989

Attest:

DONALD J. QUIGG

Attesting Officer

Commissioner of Patents and Trademarks